（12）United States Patent
Abrahamson et al.

(10) Patent No.: US 10,182,763 B1
(45) Date of Patent: Jan. 22, 2019

(54) INTELLIGENT ASSISTIVE MOBILITY DEVICE

(71) Applicant: Wheelie LLC, Hillsborough, CA (US)

(72) Inventors: Donna Abrahamson, Hillsborough, CA (US); Marie-Helene Gotcher, Hillsborough, CA (US); Elizabeth Fannon, Hillsborough, CA (US)

(73) Assignee: WHEELIE LLC, Hillsborough, CA (US)

( * ) Notice: Subject to any disclaimer, the term of this patent is extended or adjusted under 35 U.S.C. 154(b) by 188 days.

(21) Appl. No.: 15/221,576

(22) Filed: Jul. 27, 2016

Related U.S. Application Data

(60) Provisional application No. 62/197,499, filed on Jul. 27, 2015.

(51) Int. Cl.
| | |
|---|---|
| *A61B 5/00* | (2006.01) |
| *A61B 5/0205* | (2006.01) |
| *A61B 5/11* | (2006.01) |
| *A61B 5/16* | (2006.01) |
| *A61H 3/04* | (2006.01) |
| *G01G 19/50* | (2006.01) |
| *A61B 5/024* | (2006.01) |
| *A61B 5/053* | (2006.01) |

(52) U.S. Cl.
CPC ........ *A61B 5/6894* (2013.01); *A61B 5/0022* (2013.01); *A61B 5/0205* (2013.01); *A61B 5/1126* (2013.01); *A61B 5/165* (2013.01); *A61B 5/7282* (2013.01); *A61B 5/747* (2013.01); *A61H 3/04* (2013.01); *G01G 19/50* (2013.01); *A61B 5/02438* (2013.01); *A61B 5/0531* (2013.01)

(58) Field of Classification Search
CPC . A61B 5/0022; A61B 5/0205; A61B 5/02438; A61B 5/0531; A61B 5/1126; A61B 5/165; A61B 5/6894; A61B 5/7282; A61B 5/747; A61H 3/04; G01G 19/50
USPC .................................................. 600/300, 301
See application file for complete search history.

(56) References Cited

U.S. PATENT DOCUMENTS

| 9,157,742 | B1 * | 10/2015 | Fahrner | .................. G01C 21/00 |
| 2014/0275845 | A1 * | 9/2014 | Eagon | .................. A61B 5/6826 600/301 |
| 2015/0359699 | A1 * | 12/2015 | Chang | ..................... A61H 3/04 701/22 |

* cited by examiner

*Primary Examiner* — Michael Carey
(74) *Attorney, Agent, or Firm* — Kwan & Olynick LLP

(57) ABSTRACT

Provided are mechanisms and processes for an intelligent assistive mobility device. Intelligent assistive mobility devices disclosed herein may include systems including a frame having handles, a plurality of wheels, and a plurality of brakes coupled to the wheels. The frame is configured to provide a user with assistance during walking. The system also includes a motion sensor coupled to the frame. The motion sensor includes a rotary encoder configured to measure a distance traveled by the frame by measuring rotation of at least one of the plurality of wheels. The system also includes a contact interface coupled to the frame and configured to enable connectivity with a mobile device. The contact interface is further configured to enable monitoring of measurements and the detection of distress based, at least in part, on the measurements. The system further includes an application interface configured to communicate with a health and fitness application.

13 Claims, 7 Drawing Sheets

INTELLIGENT ASSISTIVE MOBILITY DEVICE

CROSS-REFERENCE TO RELATED APPLICATIONS

This application claims the benefit under 35 U.S.C. § 119(e) of U.S. Provisional Patent Application No. 62/197,499, filed on 2015 Jul. 27, which is incorporated herein by reference in its entirety for all purposes.

TECHNICAL FIELD

The present disclosure relates to mechanisms and processes directed to an intelligent assistive mobility device.

DESCRIPTION OF RELATED ART

As technology has progressed and people have become interested in their own health and fitness, various devices have been developed to help people monitor and track their health and fitness. For instance, pedometers, fitness trackers, and the like have become popular consumer products. These types of devices are typically wearable as a bracelet, band, or clip-on that attaches to clothing items. These types of devices often detect movements of the body that are then counted as steps. These steps are then recorded for the user to view and track.

Although many people can benefit from wearable pedometers or fitness trackers, people with compromised physical abilities, such as aging adults or disabled persons, may not be able to use these types of devices very easily. These people may need to use assistive devices such as walkers or wheelchairs to move around. However, these people may still be interested in improving and monitoring their health and fitness. Accordingly, there is a need for improved mechanisms for monitoring the health and fitness of people using assistive devices.

SUMMARY

Provided are various mechanisms and processes relating to an intelligent assistive mobility device.

In one aspect, which may include at least a portion of the subject matter of any of the preceding and/or following examples and aspects, an intelligent assistive mobility device system includes a frame having handles, a plurality of wheels, and a plurality of brakes coupled to the wheels. The frame is configured to provide a user with assistance during walking. The system also includes a motion sensor coupled to the frame. The motion sensor includes a rotary encoder configured to measure a distance traveled by the frame by measuring rotation of at least one of the plurality of wheels. The system also includes a contact interface coupled to the frame and configured to enable connectivity with a mobile device. The contact interface is further configured to enable monitoring of measurements and the detection of distress based, at least in part, on the measurements. The system further includes an application interface configured to communicate with a health and fitness application.

This and other embodiments are described further below with reference to the figures.

DETAILED DESCRIPTION OF EXAMPLE EMBODIMENTS

Reference will now be made in detail to some specific examples of the invention including the best modes contemplated by the inventors for carrying out the invention. Examples of these specific embodiments are illustrated in the accompanying drawings. While the present disclosure is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In addition, although many of the components and processes are described below in the singular for convenience, it will be appreciated by one of skill in the art that multiple components and repeated processes can also be used to practice the techniques of the present disclosure.

In the following description, numerous specific details are set forth in order to provide a thorough understanding of the present invention. Particular embodiments of the present invention may be implemented without some or all of these specific details. In other instances, well known process operations have not been described in detail in order not to unnecessarily obscure the present invention.

Although many people can benefit from wearable pedometers or fitness trackers, people with compromised physical abilities, such as aging adults or disabled persons, may need to use assistive devices such as walkers or wheelchairs to move around. These types of movements may not necessarily be trackable with currently available devices. Specifically, bracelets or bands that measure the cadence of a person's arm as they walk may not register movement or steps of someone who is holding onto the handles of a walker. However, these people may still be interested in improving and monitoring their health and fitness. Accordingly, various embodiments disclosed herein relate to improved mechanisms and processes for monitoring the health and fitness of people using assistive devices.

Figure 1:
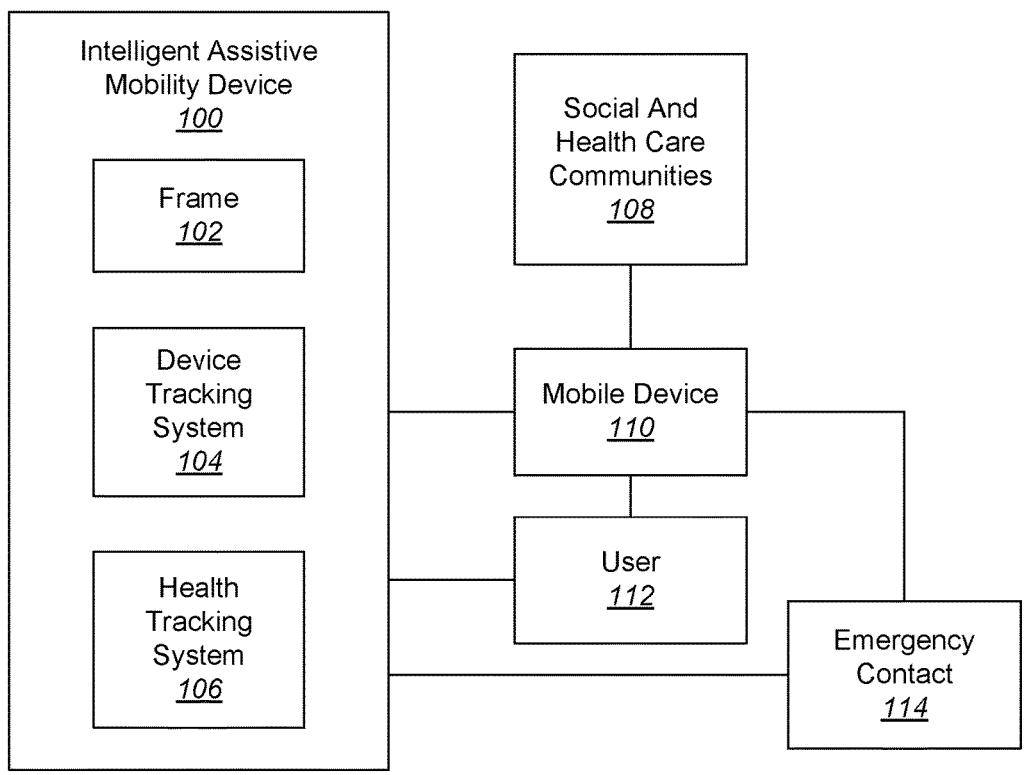
FIG. 1 illustrates an example of an intelligent assistive mobility device, configured in accordance with some embodiments.

With reference to FIG. 1, shown is one example of an intelligent assistive mobility device. In particular, the intelligent assistive mobility device 100 includes a frame 102, a device tracking system 104, and a health tracking system 106. As described below in more detail, the frame 102 that is a support structure configured to provide a user with physical assistance during walking. In particular, the user can use the frame 102 for stability during walking through the use of the frame's handles and mobility through a number of wheels attached to the frame.

As shown in the present example, the intelligent assistive mobility device 100 includes a device tracking system 104 that is designed to measure the distance traveled by the frame 102 as the user walks with the frame 102. In some embodiments, the device tracking system 104 also includes sensors configured to measure other motions of the frame 102, such as tilting, folding, etc. Tracking information detected by the device tracking system 104 is communicated through an application interface to a health and fitness application on a mobile device 110 or other computing device. This information is accessible to the user and in some examples, social and health care communities 108. The social and health care communities 108 may be linked through a social network of the health and fitness application or through a monitoring application or service. Although not indicated on the figure, the social and health care communities 108 can also include the contact 114 in some examples. In various embodiments, such contacts included in the social and health care communities 108 may include friends, family, doctors, specialists, and physical therapists.

In the present example, the intelligent assistive mobility device 100 also includes a health tracking system 106. The health tracking system includes features such as a heart monitor that measures a heart rate of the user when the user contacts at least one of the handles, a skin conductance sensor that measures a stress level of the user, and a weight sensor that measures the amount and distribution of weight that the user is applying to the frame 102. Tracking information detected by the health tracking system 106 is communicated through an application interface to a health and fitness application on a mobile device 110 or other computing device. This information is accessible to the user and in some examples, social and health care communities 108. The social and health care communities 108 may be linked through a social network of the health and fitness application or through a monitoring application or service. Although not indicated on the figure, the social and health care communities 108 can also include the contact 114 in some examples.

In the present example, the user 112 interacts with the intelligent assistive mobility device 100 through each of the frame 102, device tracking system 104, and health tracking system 106. In addition, the user 112 can interact with mobile device 110 or any other computing device used to process the tracking measurements, data, and/or perform calculations. According to various embodiments, the intelligent assistive mobility device 100 also includes a contact interface that is designed to initiate communications with or provide a notification to a contact if user distress is detected. In various embodiments, the contact interface may be configured to communicate with a mobile telecommunications device via another interface such as an application interface. The mobile device may subsequently be used to establish communications with another entity, such as a contact. As will be discussed in greater detail below, the contact interface may include a dashboard, mobile device docking location, and several buttons.

Distress can be detected in various ways. For example, the user may push a button or otherwise activate a trigger that calls the contact. In another example, distress is detected if the health tracking system 106 indicates that a particular measure or a combination of measures has exceeded a predetermined threshold. In yet another example, distress is detected if the device tracking system 104 indicates that the motion or position of the frame 102 is atypical or if the user has become detached from the frame 102 such as through a fall. In other examples, the contact can be contacted directly through an interface with the intelligent assistive mobility device 100. For instance, the frame 102 may include one or more "autodial" buttons that allows the user to contact help directly. One of these buttons can include a direct communications channel to contact 114 or other service or entity.

Figure 2:
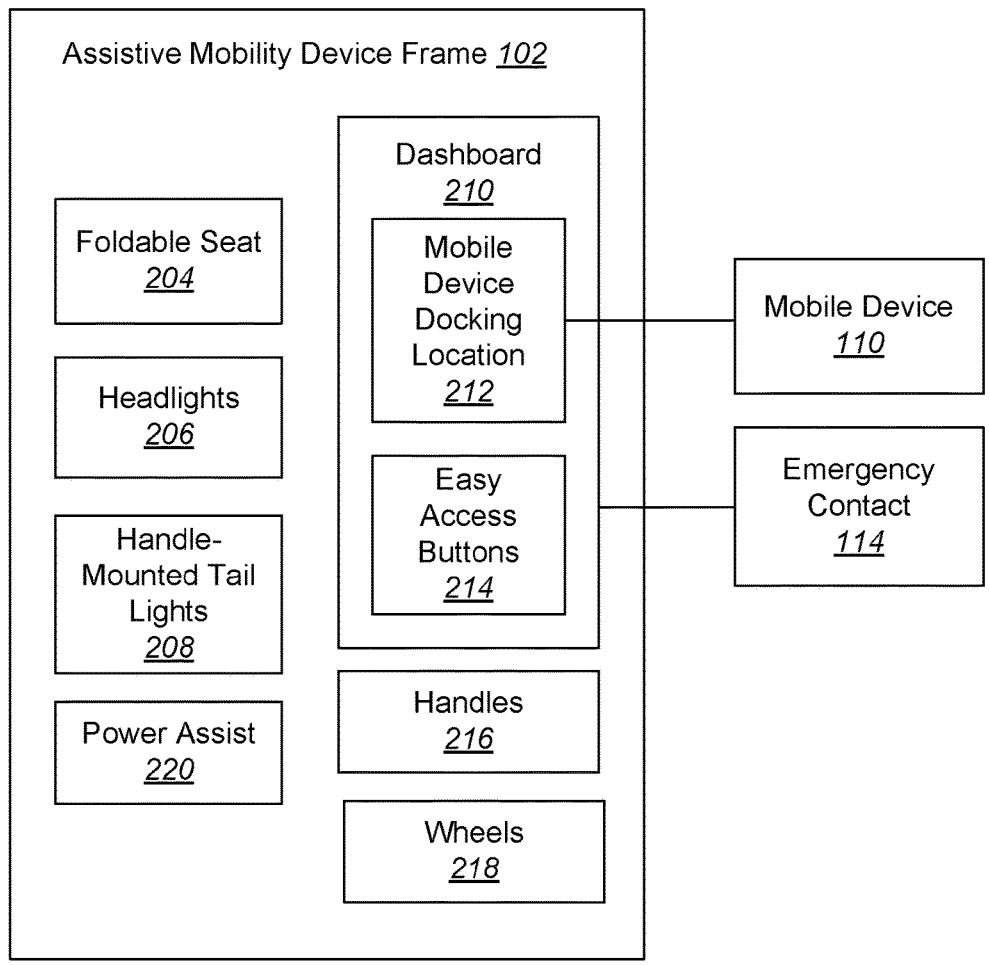
FIG. 2 illustrates an example of an assistive mobility device frame, configured in accordance with some embodiments.

With reference to FIG. 2, shown is one example of an assistive mobility device frame. In this example, the assistive mobility device frame 102 includes a foldable seat 204, headlights 206, handle-mounted tail lights 208, handles 216, wheels 218, power assist 220, and a dashboard 210. The frame 102 can be made of a variety of materials, such as carbon-fiber, aluminum, steel, titanium, or other metals or plastics. The frame 102 can be in the form of a walker with handles 216 atop a frame 102 that supports forward and downward motions while a user walks with the frame 102. The handles can include a comfortable grip and in some examples, the handles can also include sliding capability, such as on tracks, for allowing opposing arm movement when the user walks with the frame 102, thereby allowing the user to engage in a more natural gait. For instance, the handles can extend and retract from a handlebar towards the user. The handles can move forwards and backwards, while still providing support to the user. In addition, the positions of the handle bars are adjustable in some examples. For instance, the handles can include mechanisms that allow the user to easily raise and lower the handle bars. Furthermore, the handle bars can be designed to be comfortable, such as with padded or contoured grips and shapes.

In the present example, wheels 218 are included at the bottom of the frame, typically either with two wheels at the front of the frame or four wheels, one on each corner of the base of the frame. However, any number of wheels can be used. In some embodiments, the wheels can be retractable, such that the wheels can roll when pushed forward, but can retract when sufficient weight is pushed downwards on the handles to stabilize the frame if and when the user is resting or if they are trying to catch their balance. In the present embodiment, wheels 218 include tires that are selected to absorb terrain shock and to be easily maneuverable. In some instances, the tires can be colored to improve the visibility of the structure. Colored tires can also serve to personalize the structure to make it distinguishable from those of other users. Furthermore, the wheels 218 are attached to brakes that allow the user improved control and handling of the assistive mobility device frame in various examples. In some embodiments, the brakes are configured to provide resistance to the rotation of wheels 218. Accordingly, the wheels may arrest, reduce, or stop motion of frame 102. In various embodiments, brakes may be attached to front wheels, rear wheels, all wheels, or any combination of wheels 218. For example, if wheels 218 include four wheels having two front wheels and two rear wheels, brakes may be attached to all four wheels. These brakes can be designed to be easy to use and in some designs the brake cables can be hidden in the frame 102 to protect the cables and improve the simplicity of the structure and provide easy cleaning.

According to various embodiments, the frame 102 can be foldable and/or collapsible. For instance, two sides of the walker can fold into the center to create a flattened structure that is easier to store or transport. In other instances, the walker can be folded or collapsed while remaining upright and free standing. Other folding configurations are also possible. In addition, the foldable seat 204 can be folded up when stored or not in use. This foldable seat 204 can be folded down when the user wants to rest and use the frame 102 as a chair. According to various examples, the seat can lift, tilt, and be stored alongside of the frame 102. In addition, the seat can be placed at different seat heights in some examples. In addition, the seat can be made to be comfortable, such as with padding, contouring, etc.

In the present example, the assistive mobility device frame 102 also includes lighting. In particular, headlights 206 or light emitting diode (LED) strip lights are mounted to the front of the walker to both assist the user during lower light conditions and to make the walker visible to others. Any number of headlights can be used. For instance, a single headlight or multiple headlights can be used. The present example also includes tail lights 208 located on or in the ends of the handles so that they are visible from behind the walker. These tail lights 208 can be red or any other desired color. They can help make the user more visible to others. In addition, reflectors can be included on the frame 102 to improve further visibility in some examples.

According to various embodiments, assistive mobility device frame 102 includes power assist 220 for aiding the user while climbing up hills and for controlling the speed of the frame 102 when going down hills or other declines. The power assist can be implemented in a number of ways. For instance, an electric motor can be integrated with one or more of the wheels 218.

In the present embodiment, assistive mobility device frame 102 also includes a dashboard 210. The dashboard 210 includes a mobile device docking location 212 and easy access buttons 214. The mobile device docking location 212 includes a secure place to place the user's mobile device where it is easily visible and accessible. The easy access buttons 214 are auto dial easy access buttons that call particular contacts (or any desirable contacts) when pressed or otherwise activated. Any number of buttons can be used. For instance, if three buttons are provided, one can call 911, and two programmable buttons can be set to call other contacts. According to various embodiments, the easy access buttons 214 operate separately from the user's mobile device as standalone contact interfaces.

In various embodiments, the easy access buttons 214 may be configured to cause other operations and implement other functionalities as well, such as the enabling or initiation of communications with application programs that may be executed on other computing devices. For example, a user may push a button, and the button may cause a function call or application call to be sent to an application executing on a mobile device. The function call or application call may be an input that is provided to the mobile device, and may cause the mobile device to initiate an application, or may cause an application that is already executing to implement one or more functions. In one example, in response to a user pressing an easy access button on the dashboard 210, a function call may be sent to the mobile device that causes the display of the user's current geolocation using the GPS of the mobile device. In addition, the dashboard can also include a cup holder in some examples. In other examples, a cup holder can be included in another part of the frame 102.

Various design characteristics may be desirable for the assistive mobility device frame. For example, the assistive mobility device frame 102 can be designed to be lightweight and easily foldable to allow for easy use and transport. In some embodiments, the assistive mobility device frame 102 includes upright storage when folded. Another feature includes a foot piece to step on when the user goes up curbs. In addition, the assistive mobility device frame 102 can include a storage compartment, such as a pouch or box. The assistive mobility device frame 102 can include appealing design and shapes that are comfortable for the user. In addition, the assistive mobility device frame 102 can include colors that improve the visibility of the structure. Different colors can also serve to personalize the frame to make it distinguishable from those of other users.

Figure 3:
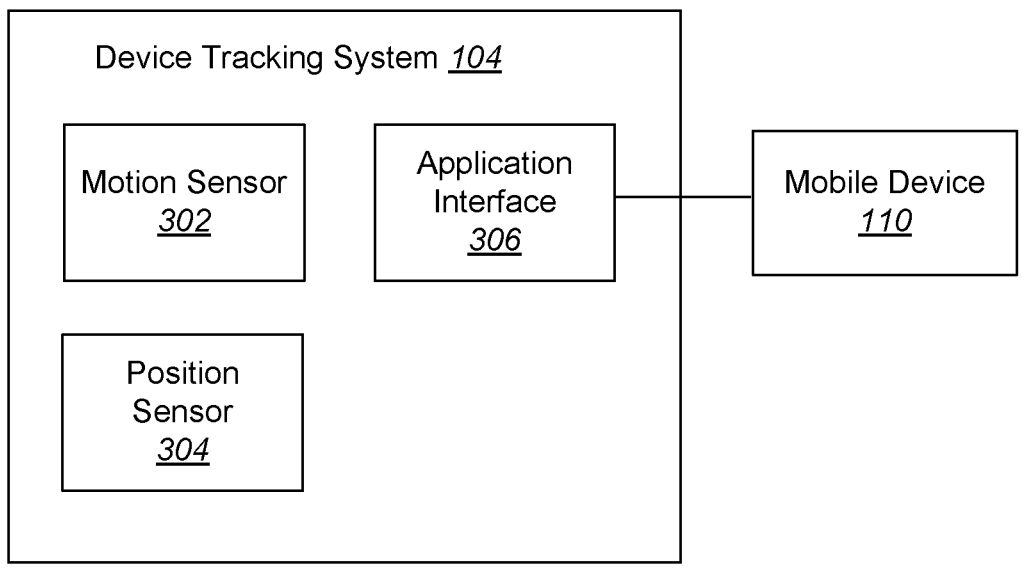
FIG. 3 illustrates an example of a device tracking system, configured in accordance with some embodiments.

With reference to FIG. 3, shown is an example of a device tracking system. The device tracking system 104 shown includes a motion sensor 302, position sensor 304, and application interface 306. The device tracking system 104 is part of the intelligent assistive mobility device 100 described with regard to FIG. 1 and is coupled to the assistive mobility device frame 102 described with regard to FIG. 2.

In the present embodiment, the motion sensor 302 is coupled to the frame and includes a rotary encoder that measures the distance traveled by the frame by measuring the rotation of at least one of the of wheels located at the bottom of the frame. In particular, the rotary encoder outputs an analog voltage based on the rotational velocity of the wheel being monitored. The analog voltage goes to an analog to digital converter that sends data to a microprocessor (e.g. embedded chip) running firmware or microcode to store the results digitally. In some embodiments, the motion sensor 302 may be an accelerometer configured to identify steps taken by a user based on sensed motion of the frame. For example, the accelerometer may detect periodic motion in one or more axes of motion, such as horizontal and/or vertical axes, where such motion is caused the user's gait and the user's movement of the frame when the frame is assisting the user. In various embodiments, the motion sensor 302 may be implemented remotely. For example, a motion sensor of another device, such as mobile device 110, may be used to track a distance traveled, and may be used to generate tracking data. Such data may be stored on mobile device 110 for subsequent processing, or may be provided to components of frame 102, such as health tracking system 106, via an application interface.

The present example also includes a position sensor 304 that tracks the upright position of the frame. The position sensor 304 turns off automatically when frame is folded, according to various examples. In the present example, an alarm sounds when the position sensor 304 indicates that the frame is not upright. In some examples, a call or text message will automatically be sent to a selected person, such as a contact, after a certain period of time following a detection that the frame is not upright.

According to various embodiments, the device tracking system 104 includes an application interface 306. For instance, the application interface 306 can be a wireless interface implementing technologies such as Bluetooth or Wifi, which allows an application on a mobile device to receive the data collected by the motion sensor 302 and the position sensor 304. As shown, the application interface 306 allows the device tracking system to communicate with an application on a mobile device 110 or other computing device. The application then renders the data in a useful form for the user. This data can be used to set and reach walking goals and observe patterns and past performance. In addition, this data can be shared in friend groups, with health professionals, and/or anyone else with whom the user wishes to share.

Although the present example is described for use with a frame as described with regard to FIG. 2, it should be noted that the device tracking system 104 can also be used with other structures, such as wheelchairs or other assistive devices. One benefit of using this type of technology with these other structures is the ability to monitor the user's routes and locations.

Figure 4:
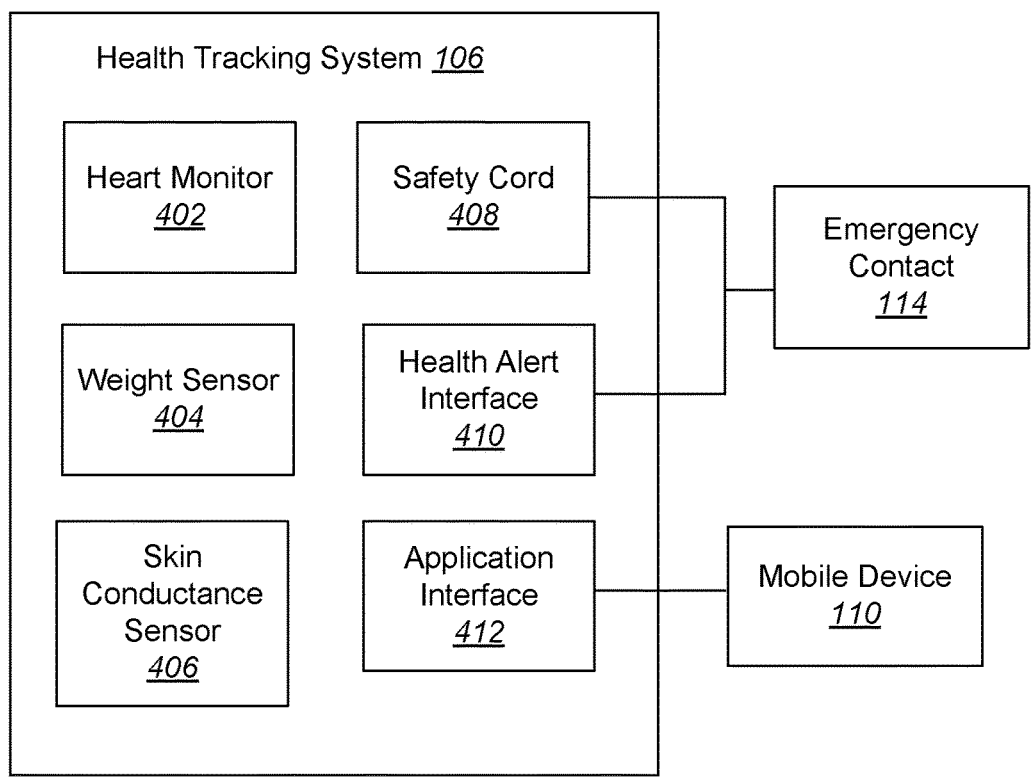
FIG. 4 illustrates an example of a health tracking system, configured in accordance with some embodiments.

With reference to FIG. 4, shown is an example of a health tracking system. The health tracking system 106 shown includes a heart monitor 402, weight sensor 404, skin conductance sensor 406, safety cord 408, health alert interface 410, and application interface 412. The health tracking system 106 is part of the intelligent assistive mobility device 100 described with regard to FIG. 1 and is coupled to the assistive mobility device frame 102 described with regard to FIG. 2.

In the present embodiment, health tracking system 106 includes numerous sensors. The heart monitor 402 measures the user's heartbeat when the user contacts the handles of the frame. In particular, an electric current is sent through both handles of the frame to receive data from the palms of the user. The weight sensor 404 includes sensors in both handles and/or sidebars that measure the amount of weight being placed on each side of the frame. This information can be used to determine the user's balance and gait. The skin conductance sensor 406 indirectly measures the user's stress level. In particular, the skin conductance sensor 406 is located on the handlebars and measures the skin's ability to conduct electricity, which tends to climb when the user is under stress.

In the present example, the health tracking system 106 includes at least a portion of contact interface, which may be configured to further include a safety cord 408 and a health alert interface 410. The safety cord 408 is an extendable cord that is removably attached to the assistive mobility device frame 102 and secured to the user when the user engages the assistive mobility device frame 102. Because the safety cord is extendable, the user can move comfortably with respect to the assistive mobility device frame 102 when walking. In some instances, the safety cord can be coupled to the assistive mobility device frame 102 through an electronic interface that is connected to the system supporting the autodial buttons. If the user becomes separated from the assistive mobility device frame 102, such as through a fall, the safety cord 408 becomes detached from the assistive mobility device frame 102. If the safety cord 408 becomes detached from the assistive mobility device frame 102, a contact will be called or texted for help as a safety function. In some examples, the contact will be contacted after the safety cord 408 has been detached for more than a specified amount of time, in order to allow the user to reattach the cord if it is accidentally removed. In other examples, an alarm will sound if the safety cord 408 has been detached.

In the present example, the health tracking system 106 also includes a health alert interface 410. In various embodiments, the health alert interface 410 may be configured to monitor measurements made by the heart monitor 402, weight sensor 404, and skin conductance sensor 406, and detect distress based, at least in part, on the various of measurements, as will be discussed in greater detail below with reference to FIG. 6. Accordingly, health alert interface 410, or one or more other components of health tracking system 106, may include various on board processing circuitry, such as a processor and memory similar to those discussed below with reference to FIG. 7. In various embodiments, processing components of a mobile device or other computing device may be used to process tracking data received from the monitors and sensors.

In some embodiments, an automatic alert, such as a text, call or email, is sent to a contact if a health concern is present, such as a dangerous heart beat or dangerous stress levels. As previously discussed, such an alert may be generated and then sent to a mobile device via application interface 412. The system can be programmed with threshold measurements that, if exceeded, would constitute a dangerous or concerning condition for the user. In various embodiments, such a dangerous condition may be defined based on one or more of a user's age, weight, resting heart rate, health conditions, or any other suitable measure.

Although the present example is described for use with a frame as described with regard to FIG. 2, it should be noted that the health tracking system 106 can also be used with other structures, such as wheelchairs or other assistive devices. One benefit of using this type of technology with these other structures is the ability to monitor the user's health and fitness levels during normal activities and movement.

Figure 5:
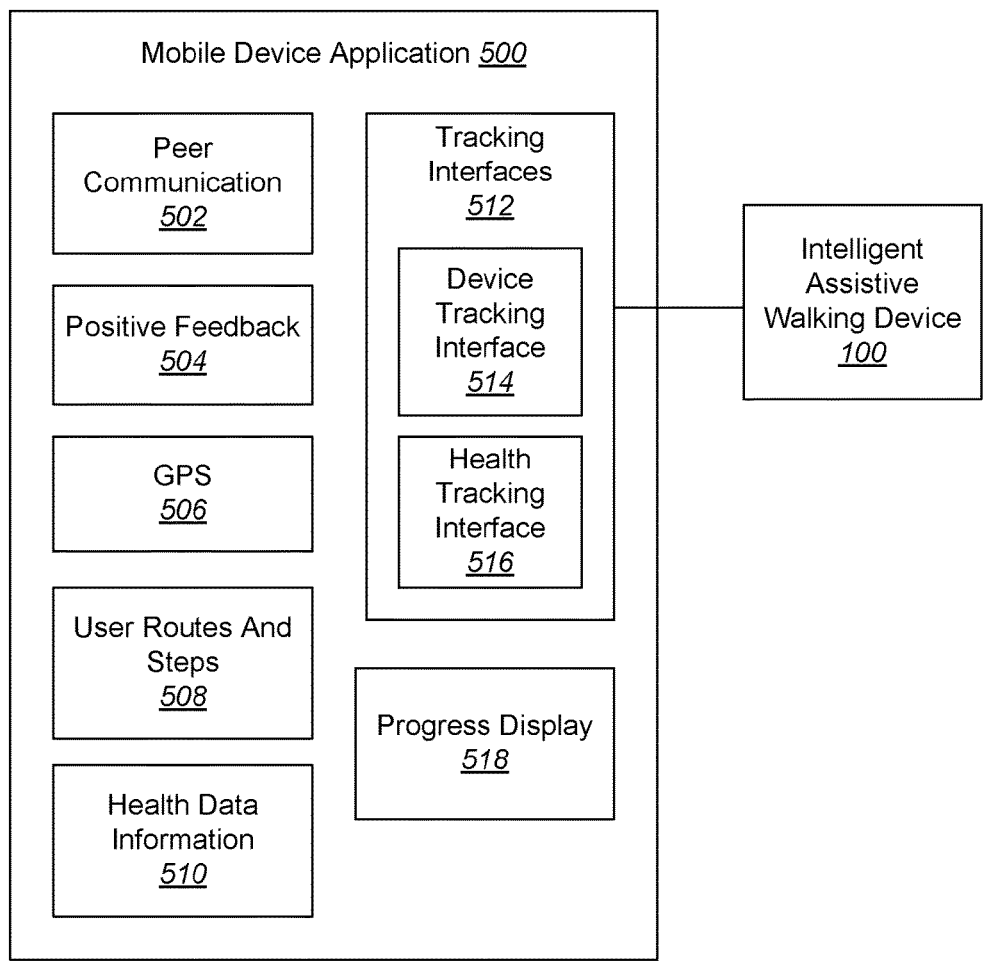
FIG. 5 illustrates an example of a mobile device application, configured in accordance with some embodiments.

With reference to FIG. 5, shown is an example of a mobile device application that can be used with the intelligent assistive mobility device. As described above with regard to various embodiments, a mobile device application 500 can communicate with an intelligent assistive mobility device 100. In particular, the mobile device application 500 can receive data through tracking interfaces 512. Specifically, the mobile device application 500 receives device tracking data through device tracking interface 514 and health tracking data through health tracking interface 516. In some examples, these interfaces can be combined.

According to various embodiments, the mobile device application 500 processes the data it receives and makes the information available to the user. For instance, the mobile device application 500 can calculate the user's routes and steps 508 from device tracking data. The routes are calculated using GPS 506 data. Because the user can dock a mobile device to the intelligent assistive mobility device 100, the GPS on the mobile device/application can be used by the mobile device application 500 to track the user's travel. In some examples, a GPS tracking device can be included in the intelligent assistive mobility device frame, which can be useful if the user forgets the mobile device. Other information related to device tracking data can also be accessible to the user. In addition, health tracking data is processed and the resulting health information is made available to the user through health data information 510. For instance, measurements for heart rate, weight application, and stress can be displayed in the form of charts, graphs, or tables for the user.

In the present example, the mobile device application 500 provides incentive features for the user. Specifically, the mobile device application 500 provides positive feedback to the user when daily goals are met. For instance, a message can be displayed such as "Good Work! You reached 2000 steps today!" In addition, a progress display 518 projects or otherwise displays various colored lights depending on the user's progress towards reaching a daily personal walking goal.

According to various embodiments, the user can share their progress with others, such as social and health care communities. In particular, peer communication 502 includes the ability to link wirelessly with others to share data, set goals, encourage each other, etc. For instance, the application can notify a circle of friends when the user achieves a goal. In another example, the user's route, including number of steps taken, can be saved and shared with a circle of friends through the application.

Figure 6:
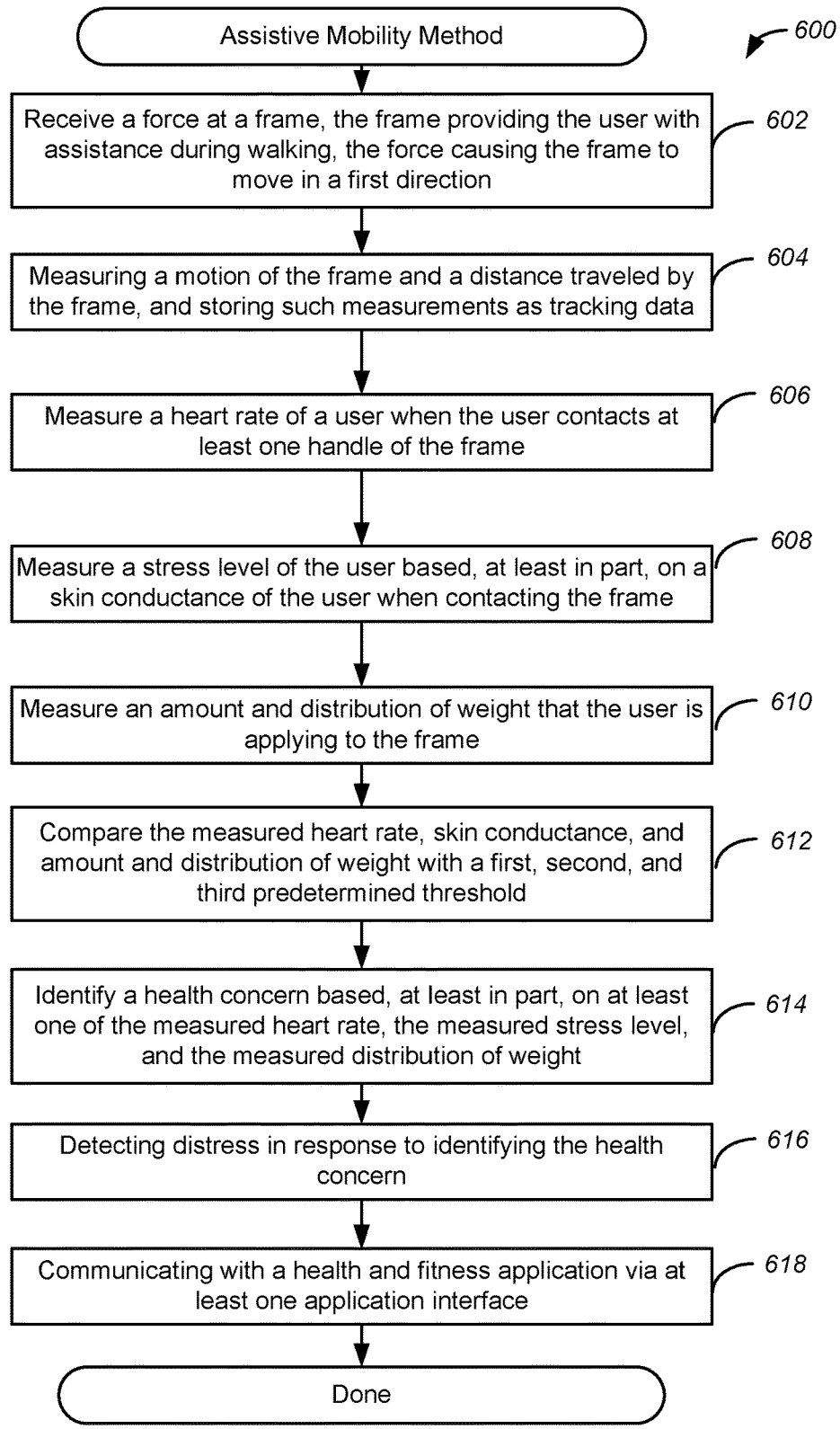
FIG. 6 illustrates a flow chart of an example of a method of using an assistive mobility device frame, implemented in accordance with some embodiments.

FIG. 6 illustrates a flow chart of an example of a method of using an assistive mobility device frame, implemented in accordance with some embodiments. As discussed above, an intelligent assistive mobility device may be utilized to provide a user with physical assistance, provide various tracking data associated with the user, as well as monitor various metrics associated with the user to detect distress of the user and initiate communications with contacts if appropriate. Accordingly, as will be discussed in greater detail below with reference to method 600, various measurements may be made by the intelligent assistive mobility device, and such measurements may be used to identify health concerns and distress events.

Accordingly, method 600 may commence with operation 602 during which a force may be received at a frame. In various embodiments, the force causes the frame to move in a first direction. For example, a user of an assistive mobility device frame may provide the force to the frame in a first direction which may be a lateral or horizontal direction when walking and using the frame for assistance. As previously discussed, the frame may include wheels, and the movement of the frame may cause rotation of the wheels.

Method 600 may proceed to operation 604 during which a motion of the frame and a distance traveled by the frame may be measured, and such measurements may be stored as tracking data. As previously discussed, the frame may include various sensors, and such sensors may be used to measure a motion of the frame. For example, the sensors may measure and analyze an ordinary gait of the user, as well as measure and identify atypical events such as an abnormal degree of tilt or folding of the frame. In some embodiments, such sensors may utilize, at least in part, a plurality of accelerometers. As also discussed above, a distance traveled by the frame may be measured based on a rotation of at least one of the wheels. Accordingly, a rotation of a wheel may be detected, measured, and translated to a linear distance traveled by the user.

Method 600 may proceed to operation 606 during which a heart rate of a user may be measured when the user contacts at least one handle of a frame. As discussed above, the frame provides the user with assistance during walking. As also discussed above, the heart rate may be measured by a heart monitor included in a health tracking system. Accordingly, the heart monitor may periodically measure and monitor the heart rate of the user, and such measurements may be included in tracking information or other data that may also be provided to a mobile device application as previously discussed.

Method 600 may proceed to operation 608 during which a stress level of the user is measured based, at least in part, on a skin conductance of the user when contacting the frame. As previously discussed, the user may be contacting a portion of the intelligent assistive mobility device, such as a handle, and a sensor may make various skin conductance measurements of the user's skin. Such measurements may also be stored as tracking information.

Method 600 may proceed to operation 610 during which an amount and distribution of weight that the user is applying to the frame may be measured. As similarly discussed above, a weight sensor may measure an amount of weight applied to the frame, may measure a distribution of weight across the frame, and may detect changes in such measurements. These measurements may also be stored as tracking information. As will be discussed in greater detail below, such data may form the basis of detecting and identifying health concerns and distress associated with the user, as well as the notification of contact responsive to such detecting.

Method 600 may proceed to operation 612 during which the measured heart rate, skin conductance, and amount and distribution of weight may be compared with a first, second, and third predetermined threshold. As previously discussed, several threshold values may have been previously determined for the particular user using the intelligent assistive mobility device. In various embodiments, the measurements obtained during operations 602, 604, and 606 may be compared with the thresholds to determine if the measurements have exceeded the thresholds. For example, the measured heart rate may be compared with the first predetermined threshold, the measured skin conductance may be compared with the second predetermined threshold, and the measured amount and distribution of weight may be compared with the third predetermined threshold.

Method 600 may proceed to operation 614 during which a health concern may be identified based, at least in part, on at least one of the measured heart rate, the measured stress level, and the measured distribution of weight. In various embodiments, the health concern is identified based on the comparison performed during operation 608. In some embodiments, the health concern may be identified in response to any of the measurements exceeding their respective thresholds. For example, the health concern may be identified in response to the measured heart rate exceeding the first threshold. In various embodiments, the health concern may be identified in response to two or more of the measurements exceeding their respective thresholds. For example, a health concern may be identified if the measured heart rate and measured skin conductance exceed the first threshold and second threshold. In some embodiments, different health concerns may be identified in response to different instances or combinations of threshold crossings.

Method 600 may proceed to operation 616 during which distress may be detected in response to identifying the health concern. As discussed above, the detection of distress may trigger or initiate the implementation of one or more operations. For example, one or more contacts may be contacted in response to the detection of the distress. As also discussed above, such contacting may occur automatically. In this way, contact with people, such as health care professionals, may be initiated automatically in response to the detection of distress of a user and the identifying of a health concern based on the previously described data.

Method 600 may proceed to operation 616 during which a health and fitness application may be communicated with. As similarly discussed above, a health and fitness application may be used to provide connectivity between the user of the frame and other entities such as social and health care communities via one or more social networks or other channels of communication. Accordingly, during operation 616, various data and information, such as measurements and tracking data or information, may be sent to the health and fitness application via one or more communications interfaces. The health and fitness application, which may be run on a mobile device, may utilize the data to generate and render a display that is presented to the user of the frame.

Figure 7:
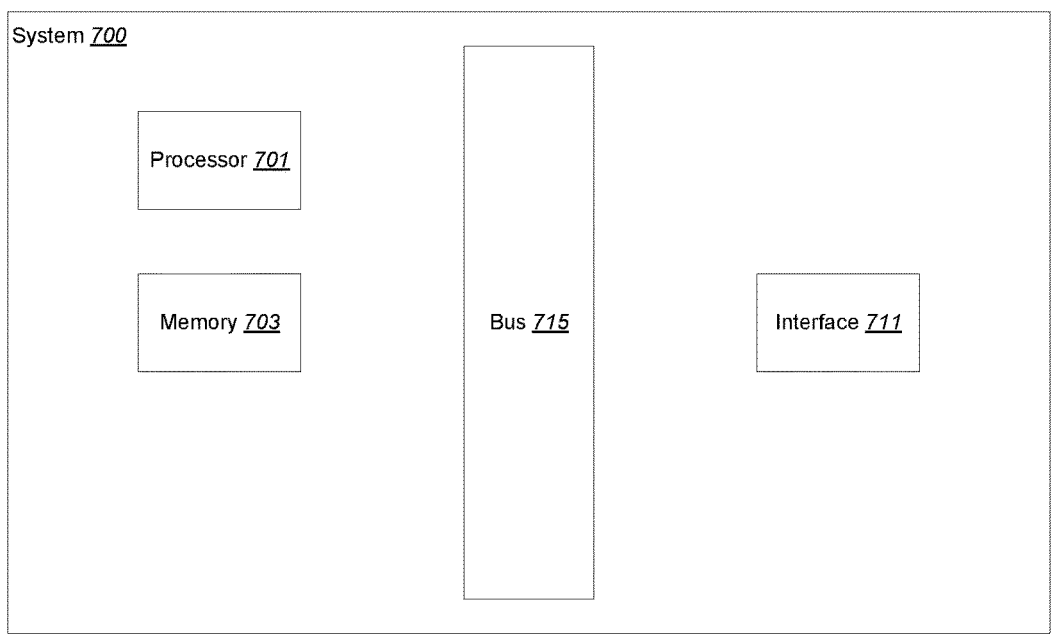
FIG. 7 illustrates an example of a computer system that can be used with various embodiments of the present invention.

With reference to FIG. 7, shown is a particular example of a computer system that can be used to implement particular examples of the present invention. For instance, the computer system 700 can be used to implement a mobile application for use with an intelligent assistive mobility device according to various embodiments described above. In addition, the computer system 700 shown can represent a computing system on a mobile device or on a traditional computer or laptop, etc. According to particular example embodiments, a system 700 suitable for implementing particular embodiments of the present invention includes a processor 701, a memory 703, an interface 711, and a bus 715 (e.g., a PCI bus). The interface 711 may include separate input and output interfaces, or may be a unified interface supporting both operations. When acting under the control of appropriate software or firmware, the processor 701 is responsible for such tasks such as optimization. Various specially configured devices can also be used in place of a processor 701 or in addition to processor 701. The complete implementation can also be done in custom hardware. The interface 711 is typically configured to send and receive data packets or data segments over a network. Particular examples of interfaces the device supports include Ethernet interfaces, frame relay interfaces, cable interfaces, DSL interfaces, token ring interfaces, and the like.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the system 700 uses memory 703 to store data and program instructions and maintain a local side cache. The program instructions may control the operation of an operating system and/or one or more applications, for example. The memory or memories may also be configured to store received metadata and batch requested metadata.

Because such information and program instructions may be employed to implement the systems/methods described herein, the present invention relates to tangible, machine readable media that include program instructions, state information, etc. for performing various operations described herein. Examples of machine-readable media include hard disks, floppy disks, magnetic tape, optical media such as CD-ROM disks and DVDs; magneto-optical media such as optical disks, and hardware devices that are specially configured to store and perform program instructions, such as read-only memory devices (ROM) and programmable read-only memory devices (PROMs).

Examples of program instructions include both machine code, such as produced by a compiler, and files containing higher level code that may be executed by the computer using an interpreter.

While the present disclosure has been particularly shown and described with reference to specific embodiments thereof, it will be understood by those skilled in the art that changes in the form and details of the disclosed embodiments may be made without departing from the spirit or scope of the invention. Specifically, there are many alternative ways of implementing the processes, systems, and apparatuses described. It is therefore intended that the invention be interpreted to include all variations and equivalents that fall within the true spirit and scope of the present invention. Moreover, although particular features have been described as part of each example, any combination of these features or additions of other features are intended to be included within the scope of this disclosure. Accordingly, the embodiments described herein are to be considered as illustrative and not restrictive.

What is claimed is:

1. A system comprising:
  a frame having handles, a plurality of wheels, and a plurality of brakes coupled to the plurality of wheels, the frame configured to provide a user with assistance during walking;
  a motion sensor coupled to the frame, the motion sensor including a rotary encoder configured to measure a distance traveled by the frame by measuring rotation of at least one of the plurality of wheels;
  a contact interface coupled to the frame, wherein the contact interface is configured to enable connectivity with a mobile device, and is further configured to enable the monitoring of a plurality of measurements and the detection of distress based, at least in part, on the plurality of measurements;
  a health tracking system coupled to the frame, the health tracking system comprising a heart monitor that measures a heart rate of the user when the user contacts at least one of the handles, a skin conductance sensor that measures a stress level of the user, and a weight sensor that measures an amount and distribution of weight that the user is applying to the frame,
  wherein the health tracking system is configured to identify a health concern based on at least one of the measured heart rate, stress level, and amount and distribution of weight applied to the frame, wherein the health concern is identified based on a comparison of at least one of the measured heart rate, stress level, and amount and distribution of weight applied to the frame with at least one of a plurality of predetermined thresholds;
  wherein the health tracking system is further configured to detect distress based, at least in part, on the identified health concern; and
  an application interface configured to communicate with a health and fitness application.

2. The system of claim 1, wherein the health and fitness application is configured to run on a mobile device or other computing device.

3. The system of claim 2, wherein the health and fitness application is configured to enable social and health care communities to view tracking information associated with the user.

4. The system of claim 3, wherein the social and health care communities include a circle of friends.

5. The system of claim 1, wherein the contact interface includes a plurality of buttons configured to communicate with an application executed on the mobile device in response to the user pushing at least one of the plurality of buttons.

6. The system of claim 1, wherein the contact interface includes a plurality of buttons configured to enable communication between the user and social and health care communities in response to the user pushing at least one of the plurality of buttons.

7. The system of claim 1, wherein the health concern is indicated if the heart monitor detects a heart rate that exceeds a predetermined threshold.

8. The system of claim 1, wherein the health concern is indicated if the skin conductance sensor indicates a stress level that exceeds a predetermined threshold.

9. The system of claim 1, wherein the health concern is indicated if the weight sensor indicates an amount and distribution of weight applied by the user that exceeds a predetermined threshold.

10. A device comprising:
  a frame having handles, a plurality of wheels, and a plurality of brakes coupled to the plurality of wheels, the frame configured to provide a user with assistance during walking;
  one or more processors configured to:
    receive measurements of a motion of the frame and store such measurements as tracking data;

receive measurements of a distance traveled by the frame and store such measurements in the tracking data, the distance being determined based on a measurement of a rotation of at least one of the plurality of wheels;

receive a plurality of measurements comprising a heart rate of the user when contacting at least one of the handles, a stress level of the user based on at least one of the heart rate and a skin conductance of the user, and an amount and distribution of weight that the user is applying to the frame;

identify a health concern based on at least one of the measured heart rate, stress level, and amount and distribution of weight applied to the frame, wherein the health concern is identified based on a comparison of at least one of the plurality of measurements with at least one of a plurality of predetermined thresholds;

detect distress based, at least in part, on the identified health concern; and communicate with a health and fitness application via at least one application interface.

11. The device of claim 10, wherein the health and fitness application is configured to run on a mobile device or other computing device, and wherein the health and fitness application is configured to enable social and health care communities to view tracking information associated with the user.

12. A method comprising:

receiving a force at a frame having handles and a plurality of wheels, the frame providing a user with assistance during walking, the force causing the frame to move in a first direction;

measuring, via a motion sensor, a motion of the frame and storing such measurements as tracking data;

measuring a distance traveled by the frame and storing such measurements in the tracking data, the distance being determined based on a rotation of at least one of a plurality of wheels included in the frame;

measuring, using a plurality of sensors of a health tracking system, a heart rate of the user when the user contacts at least one of the handles, a skin conductance associated with a stress level of the user, and an amount and distribution of weight that the user is applying to the frame;

identifying, using the health tracking system, a health concern based on at least one of the measured heart rate, stress level, and amount and distribution of weight applied to the frame, wherein the health concern is identified based on a comparison of at least one of the measured heart rate, stress level, and amount and distribution of weight applied to the frame with at least one of a plurality of predetermined thresholds;

detecting, using the health tracking system, distress based, at least in part, on the identified health concern; and communicating with a health and fitness application via at least one application interface, the communicating providing the tracking data to the health and fitness application.

13. The method of claim 12, wherein the health and fitness application runs on a mobile device or other computing device, and wherein the health and fitness application enables social and health care communities to view tracking information associated with the user.

* * * * *